(12) United States Patent
Blakemore et al.

(10) Patent No.: US 8,608,747 B2
(45) Date of Patent: Dec. 17, 2013

(54) BUR GUIDE ATTACHMENT AND METHOD OF USE

(75) Inventors: David Blakemore, Warsaw, IN (US); Eric M. Lucas, Clemson, SC (US); Keith E. Pennington, Warsaw, IN (US)

(73) Assignee: Vot, LLC, Warsaw, IN (US)

( * ) Notice: Subject to any disclaimer, the term of this patent is extended or adjusted under 35 U.S.C. 154(b) by 178 days.

(21) Appl. No.: 13/251,359

(22) Filed: Oct. 3, 2011

(65) Prior Publication Data
US 2012/0083788 A1    Apr. 5, 2012

Related U.S. Application Data

(60) Provisional application No. 61/388,828, filed on Oct. 1, 2010.

(51) Int. Cl.
*A61F 5/00*    (2006.01)
(52) U.S. Cl.
USPC .............................. 606/87; 606/79; 606/180
(58) Field of Classification Search
USPC .............. 606/79, 80, 87–89, 180; 408/239 A, 408/241 G, 241 S
See application file for complete search history.

(56) References Cited

U.S. PATENT DOCUMENTS

| 8,114,083 B2 * | 2/2012 | Haines | 606/79 |
| 2008/0279648 A1 * | 11/2008 | Campbell | 408/239 A |

* cited by examiner

*Primary Examiner* — Andrew Yang
(74) *Attorney, Agent, or Firm* — Heslin Rothenberg Farley & Mesiti PC

(57) ABSTRACT

The invention provides a guide for controlling a surgical instrument, that includes a cutting member configured to resect a portion of anatomy and a sheath. The sheath may have a circular connecting portion with an inner diameter substantially the same as the outer diameter of the surgical instrument to receive the surgical instrument. The sheath may also include at least two distally extending arms connected to the circular connecting portion and a ring connected to the distal portion of the at least two distally extending arms. The sheath may also include a distally extending extension connected to the ring. The guide has a superiorly extending guard connected to the distal portion of the extension and a projection member positioned on a superior surface of the guard. The projection member includes a generally circular base and circular platform that has a diameter larger than the generally circular base.

19 Claims, 7 Drawing Sheets

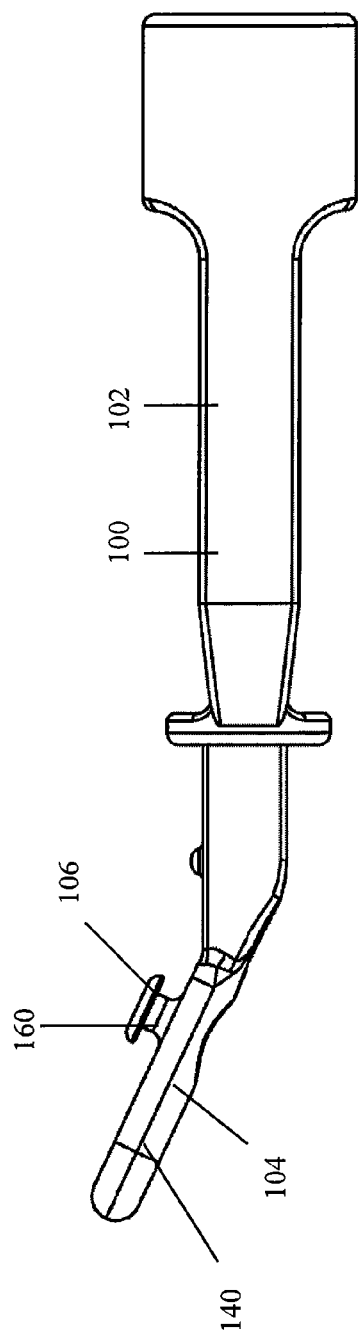
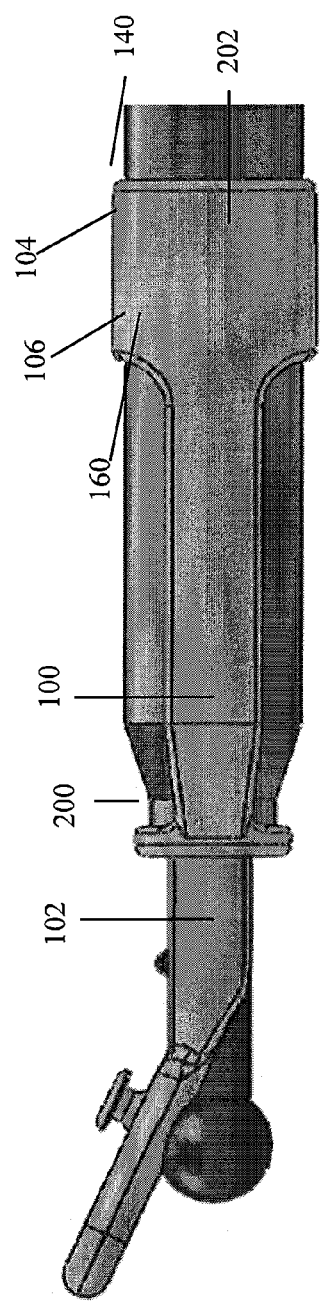
FIG. 1
FIG. 2

BUR GUIDE ATTACHMENT AND METHOD OF USE

CROSS REFERENCE TO RELATED APPLICATION

This application is related to U.S. provisional patent application No. 61/388,828 filed on Oct. 1, 2010, the entirety of which is hereby incorporated by reference.

TECHNICAL FIELD

This invention relates generally to the field of surgical instruments, and more specifically, to the field of attachments to guide and control the motion of surgical instruments.

BACKGROUND OF THE INVENTION

Surgical procedures often require the removal of a section of bone in order to make room for an implant. In these procedures it is often necessary to remove only a specific area of the bone without harming or damaging the remaining bone stock. Any damage to the surrounding bone can compromise or weaken the remaining bone and subsequent bone-implant interface. However, it is often difficult to visualize the precise area of the bone to be resected and bone cutting tools can be difficult to control and may kick away from the desired path unexpectedly. The use of cutting devices can result in resections that are too deep, improperly shaped, have the wrong orientation, or are in the wrong location, damaging surrounding tissue. Therefore, it is difficult to remove the proper amount and area of bone necessary for the implant.

One attempt to limit the area of bone resected in freehand operations has included a metal template. The template includes a metal rim that is placed over the section of bone to be resected, with an inner area defining the portion of bone to be removed. The surgeon must then resect within the rim. However, contact with the rim can result in unwanted debris in the implantation site. The rim may also be bent or improperly placed, leading to an improperly shaped implant site. The metal rim is also bulky and awkward to implement as the template has to be larger than the area to be resected.

Computerized systems have been developed that are capable of automatically resecting a bone. These computerized systems perform image guided surgery and rely on bone images and anatomical landmarks. The computerized systems are expensive, and can still result in improperly shaped resections, particularly resections that are too deep.

SUMMARY OF THE INVENTION

The invention provides, in a first aspect, a guide for controlling a surgical instrument, the surgical instrument including a cutting member configured to resect a portion of anatomy. The guide may include a sheath. The sheath may include a circular connecting portion with an inner diameter substantially the same as an outer diameter of the surgical instrument. The circular connecting portion may be configured to receive the surgical instrument. The sheath may also include at least two distally extending arms connected to the circular connecting portion. The sheath may include a ring connected to the distal portion of the at least two distally extending arms. The sheath may also include an extension connected to the ring and distally extending along the surgical instrument. The guide may also include a guard connected to the distal portion of the extension, the guard extending superior to the cutting member of the surgical instrument. The guide may include a projection member positioned on a superior surface of the guard. The projection member may include a generally circular base and a generally circular platform having a diameter larger than the diameter of the generally circular base.

In an alternative embodiment, the guard may include a generally planar inferior surface, the inferior surface provided to move along a surface of a bone and resist rotational forces. The guard of the guide may extend beyond the cutting member of the surgical instrument in a distal direction. The guard may include a rounded edge, the rounded edge provided to prevent contact with other surgical implements and reduce the generation of debris during a surgical procedure. The guide may include a projection member positioned superior to the cutting member of the surgical instrument. The projection may be positioned in a proximal direction from the cutting member of the surgical instrument. The projection may be positioned in a distal direction for the cutting member of the surgical instrument. In an alternative embodiment of the guide, the guard may have a recessed portion with a depth that receives the cutting member. The depth of the recessed portion may determine the depth of the cutting member that may penetrate into a bone. The sheath of the guide may comprise a flexible material configured to deform to the shape and size of the surgical instrument. In another embodiment, the guide may also include a controlling member configured to be removably engaged with the projection member and removably attached to a portion of anatomy. The controlling member may be a tether. The tether may have a first end and a second end, a slot formed on the first end sized to receive the projection member and a slot on the second end configured to receive a fastener attached to a portion of anatomy. The tether may be a length substantially equal to a diameter of the desired resection pathway. The tether may be made from a flexible material.

In another aspect of the invention, a guide for controlling a surgical instrument is provided. The surgical instrument includes a cutting member configured to resect a portion of anatomy. The guide may include a generally cylindrical connecting portion with an inner diameter substantially the same as an outer diameter of the surgical instrument. The cylindrical connecting portion may be configured to receive the surgical instrument. The guide may also include at least one distally extending arm connected to the generally cylindrical connecting portion. The guide may also include a vertical member attached to the distal end of the distally extending arm. A head may be formed on the superior portion of the vertical member. In another embodiment, the guide may include a vertical member positioned in a superior direction from the cutting member. The vertical member may be position in a proximal direction from the cutting member in another embodiment. The guide may also include a frame, the frame including at least one aperture configured to receive at least one fastener to secure the frame to a bone. The frame may also include at least to rails and the at least two rails may form at least one passageway. The frame may also include at least one aperture in communication with the at least one passageway, the at least one aperture configured to receive the head. In another embodiment, the guide may be removable coupled to the frame and the vertical member may be disposed within the at least one passageway. In another embodiment, the at least one distally extending arm may be a substantially planar member.

According to another aspect of the invention, a method of performing a surgery is provided. The method may include selecting a surgical instrument including a cutting member configured to resect a portion of anatomy. The method may include selecting a guide. The guide may include a sheath. The sheath may include a circular connecting portion with an inner diameter substantially the same as an outer diameter of the surgical instrument. The circular connecting portion may be configured to receive the surgical instrument. The sheath may also include at least two distally extending arms connected to the circular connecting portion. The sheath may include a ring connected to the distal portion of the at least two distally extending arms. The sheath may also include an extension connected to the ring and distally extending along the surgical instrument. The guide may also include a guard connected to the distal portion of the extension, the guard extending superior to the cutting member of the surgical instrument. The guide may include a projection member positioned on a superior surface of the guard. The projection member may include a generally circular base and a generally circular platform having a diameter larger than the diameter of the generally circular base.

The method may also include selecting a tether including a first end and a second end, the first end including a first slot formed thereon, the first slot sized to receive the projection member, the second end including a second slot, the second slot configured to receive a fastener attached to the portion of anatomy. The method may include disposing the sheath about the surgical instrument. The method may also include inserting the projection member through the first end of the tether. The method may also include inserting the fastener through the second end of the tether. The method may also include operating the surgical instrument in a manner controlled by the guide and the tether to perform a resection on the portion of anatomy.

Other additional features and benefits will become apparent from the following drawings and descriptions of the invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the end of the specification. The foregoing and other objects, features, and advantages of the invention are apparent from the following detailed description taken in conjunction with the accompanying drawings in which:

FIG. 1 is a side elevation view of one embodiment of a bur guide attachment, in accordance with an aspect of the invention;

FIG. 2 is a side elevation view of the bur guide attachment of FIG. 1, attached to a burring device, in accordance with an aspect of the invention;

DETAILED DESCRIPTION FOR CARRYING OUT THE INVENTION

Figure 3:
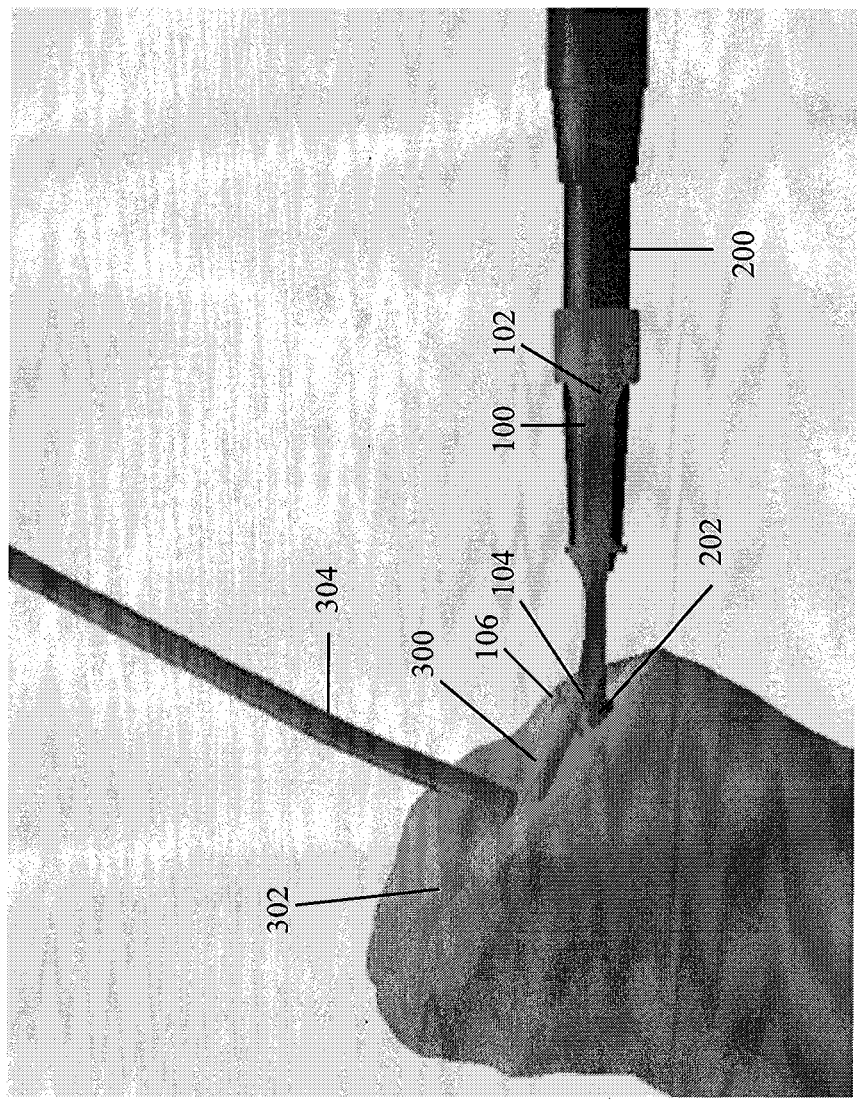
FIG. 3 is a perspective view of the bur guide attachment of FIG. 1, attached to a burring device and a controlling device, and brought into proximity with a bone, in accordance with an aspect of the invention.

For the purposes of promoting an understanding of the principles of the bur guide attachment, reference will now be made to the embodiments, or examples, illustrated in the drawings and specific language will be used to describe these. It will nevertheless be understood that no limitation of the scope of the invention is thereby intended. Any alterations and further modifications in the described embodiments, and any further applications of the principles of the invention as described herein are contemplated as would normally occur to one skilled in the art to which the bur guide attachment invention relates.

In this detailed description and the following claims, the words proximal, distal, anterior, posterior, medial, lateral, superior and inferior are defined by their standard usage for indicating a particular part of a surgical instrument or surgical opening according to the relative disposition of the surgical instrument, surgical opening or directional terms of reference. For example, "proximal" means the portion of the surgical instrument positioned nearest the torso while "distal" indicates the part of the surgical instrument farthest from the torso. As for directional terms, "anterior" is a direction towards the front side of the body, "posterior" means a direction towards the back of the body, "medial" means towards the midline of the body, "lateral" is a direction towards the sides or away from the midline of the body, "superior" means a direction above, and "inferior" means a direction below another object or structure.

Referring now to FIG. 1, an embodiment of a bur guide attachment 100 is shown having a sheath 102, a guard 104 attached to the sheath 102, and a projection 106 attached to guard 104. Sheath 102 may be configured to fit over and around a surgical instrument. The profile of the surgical instrument may not be significantly increased because the space between bones, surgical incisions, and surgical sites generally are small and unable to accommodate large instrumentation. Thus, sheath 102 may be configured to approximate the size and shape of a surgical instrument, without significantly altering the overall profile of the surgical instrument.

Sheath 102 may be configured to be removably attached to a surgical instrument. In various embodiments, sheath 102 may be attached with a press-fit, a collet, threaded screw, or other known means of attaching sheath 102 to a surgical instrument. In still other embodiments, the bur guide attachment 100 may have a c-shaped clip, locking rail, or other known means of attachment in place of sheath 102. The sheath 102 controls the surgical instrument, and prevents rotation of the instrument relative to the sheath 102 and the surface the instrument is operating on. In one embodiment, the sheath 102 entirely prevents the rotation of the burring device. Therefore, only one section of the surgical instrument is used, reducing the probability of unwanted motion of the surgical instrument. The sheath 102 may also be configured to limit the depth the surgical instrument may be inserted into the patient's anatomy.

Now referring to FIGS. 1-3, Guard 104 may be configured to prevent unwanted twisting or rotation of the surgical instrument during a procedure. A user may only be permitted to move the surgical instrument as far as guard 104 will allow. Thus, the guard 104 comes into contact with the patient's anatomy and prevents the surgical instrument from penetrating more than the desired amount. The guard 104 may be configured so that guard 104 comes into contact with a bone 302, and thereby prevents unwanted twisting of the surgical instrument, as the twisting is resisted by the contact between guard 104 and a bone 302. Guard 104 has an edge 140 which may prevent contact between the surgical instrument and a controlling device 300, particularly where controlling device 300 is a tether, as discussed below. Guard 104 may also be configured so that the guard may not catch on the bone or any other tissue near the surgical site. Guard 104 may be configured such that edge 140 may be smooth and rounded, preventing catches on the surrounding tissue. The guard 104 may be also configured with a width at edge 140 that may be sufficient to prevent unintended contact between the surgical instrument and the controlling device, as that could result in debris entering the wound, or controlling device 300 being severed.

Now referring to FIGS. 2 and 3, the bur guide attachment 100 of FIG. 1, is shown where the sheath 102 is disposed about a burring device 200. Bur guide attachment 100 may be positioned on burring device 200 such that guard 104 and projection 106 are superior to a bur 202 of the burring device 200. Projection 106 may be a disk with a neck 160 formed between the projection 106 and guard 104. In alternative embodiments projection 106 may be a hook, a loop, or any other projection which a controlling device 300 as described below may be placed around. Projection 106 may be configured so that it may be securely disposed within controlling device 300. The burring device 200 may then be operated and moved through a patient's anatomy, but may be restrained by controlling device 300 and bur guide attachment 100. In one embodiment, the controlling device 300, in conjunction with the bur guide attachment 100, limits the depth and location of a resection.

Referring now to FIG. 3, the bur guide attachment 100 is again shown positioned on burring device 200. A controlling device 300 may be disposed about the projection 106. An example of controlling device 300 is a tether. Controlling device 300 may also be secured to a bone 302 with a fixation means 304. Fixation means 304 may be a surgical instrument as shown in FIG. 3, but in alternative embodiments, the fixation means 304 may also include a screw, bolt, pin, wire, glue, cement, or other known means of surgically affixing an object. The burring device 200 may be brought into proximity with bone 302. The burring device 200 may then be operated to resect a portion of bone 302. The resection of bone 302 may be limited by the bur guide attachment 100 and the controlling device 300.

Figure 5:
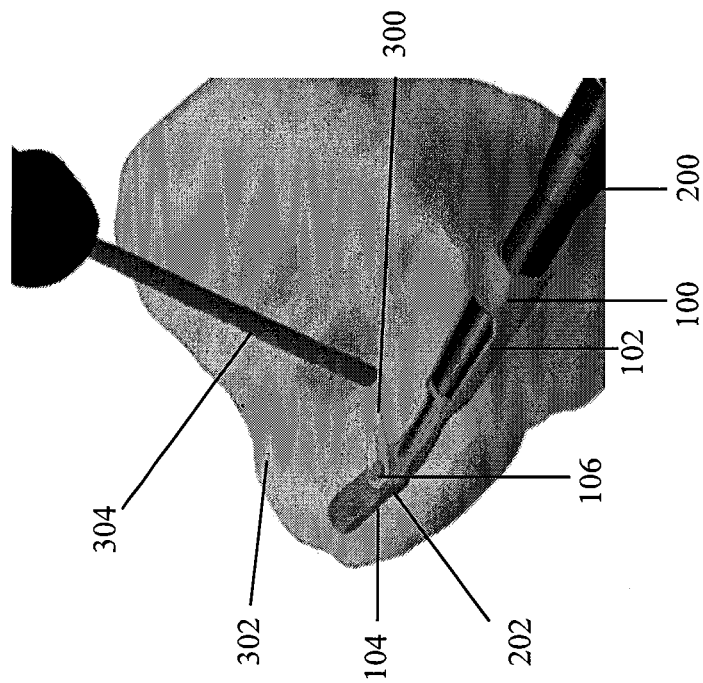
FIG. 5 is a perspective view of the bur guide attachment of FIG. 1, attached to a burring device and a controlling device, and brought into proximity with a bone where the burring device has been moved from a first position to a second position, in accordance with an aspect of the invention.
Figure 4:
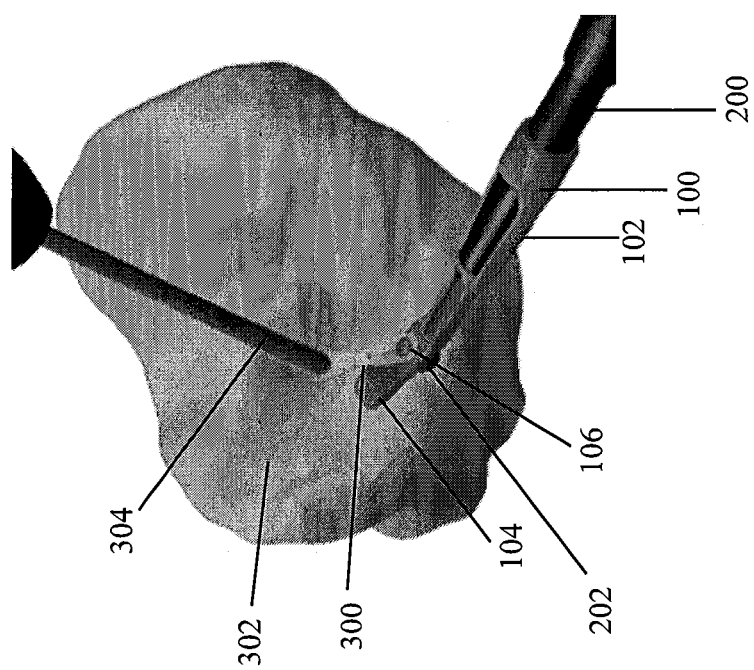
FIG. 4 is a perspective view of the bur guide attachment of FIG. 1, attached to a burring device and a controlling device, and brought into proximity with a bone, where the burring device is operated in a first position, in accordance with an aspect of the invention.

Referring now to FIGS. 4-5, the burring device 200 is shown in proximity with bone 302. Burring device 200 has been moved from a first position, shown in FIG. 4 to a second position, shown in FIG. 5. The burring device 200 moves in a generally arcuate pattern, and may be guided by the controlling device 300. In alternative embodiments, the controlling device 300 may permit the burring device 200 to move in a generally non-arcuate fashion. Once the burring device 200 has been moved over bone 302, the bur device 200, bur guide attachment 100, controlling device 300 and fixation means 304 may all be removed from bone 302. A surgeon may then perform any additional steps to complete the procedure as necessary.

The guard 104 and sheath 102 interact with bone 302 and controlling device 300 to create a surgical resection of bone 302 that has the desired shape, dimensions, orientation and depth. The guard 104 limits the depth by contacting bone 302. The projection 106 disposed within controlling device 300 ensures that the burring device 200 does not stray outside of the target resection area, resulting in the proper shape and dimensions.

In the embodiments shown in FIGS. 3-5, the burring device 200, bur guide attachment 100 and controlling device 300 are shown in proximity to the proximal tibia. The burring device shown in FIGS. 3-5 may be used, for example, to create a resection for a tibial tray implant, often associated with unicondylar and total knee replacements. In alternative embodiments, the burring device 200, bur guide attachment 100 and controlling device 300 may be used on other bones of a patient's anatomy.

Figure 6:
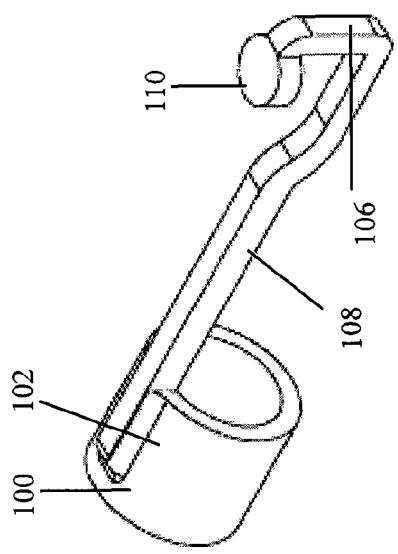
FIG. 6 is a perspective view of an alternative embodiment of the bur guide attachment of FIG. 1, in accordance with an aspect of the invention.
Figure 10:
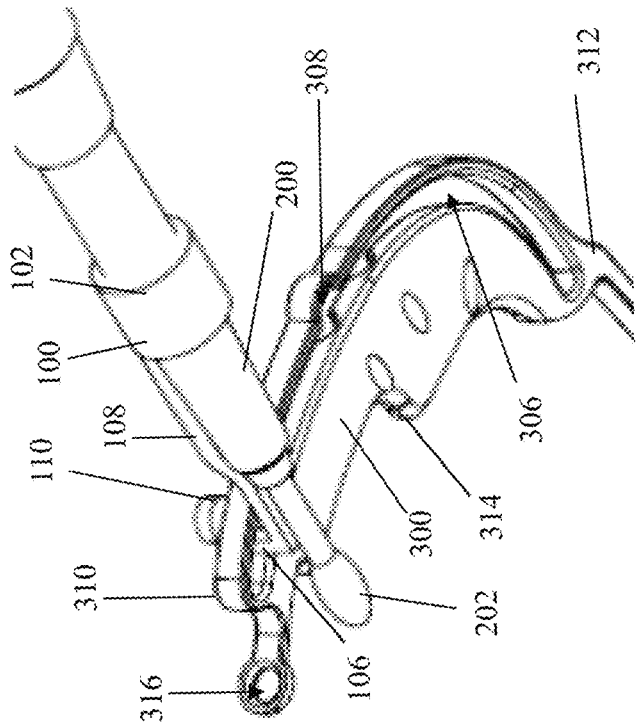
FIG. 10 is a perspective view of the bur guide attachment of FIG. 6, attached to a burring device and disposed within a controlling device, where the burring device has been moved to a first end, in accordance with an aspect of the invention.

Referring now to FIG. 6, an alternative embodiment of bur guide attachment 100 is shown, where the bur guide attachment 100 has a sheath 102, a member 108 attached to sheath 102, and a projection 106 attached to member 108. A stop 110 may be attached to projection 106. Sheath 102 may be configured to be removably attached to a surgical instrument. In various embodiments, sheath 102 may have a press-fit, a collet, threaded screw, or other known means of attaching sheath 102 to a surgical instrument. In still other embodiments, the bur guide attachment 100 may have a c-shaped clip, locking rail, or other known means of attachment may be substituted for sheath 102.

Figure 7:
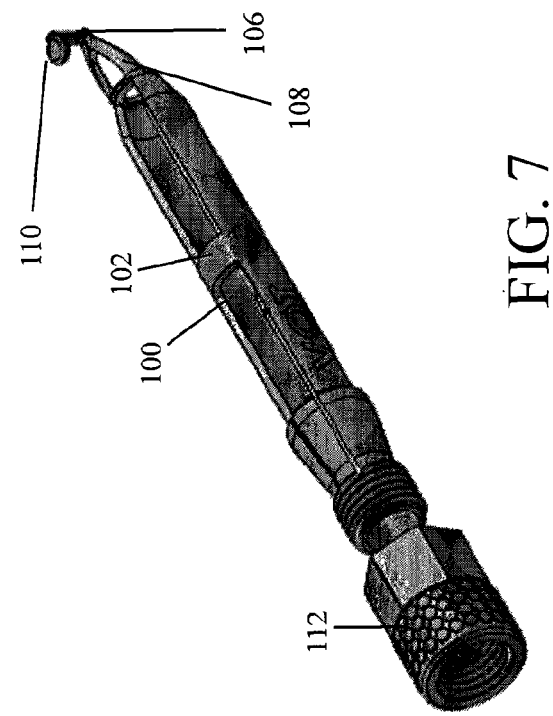
FIG. 7 is a perspective view of an alternative embodiment of the bur guide attachment of FIG. 6, in accordance with an aspect of the invention.
Figure 8:
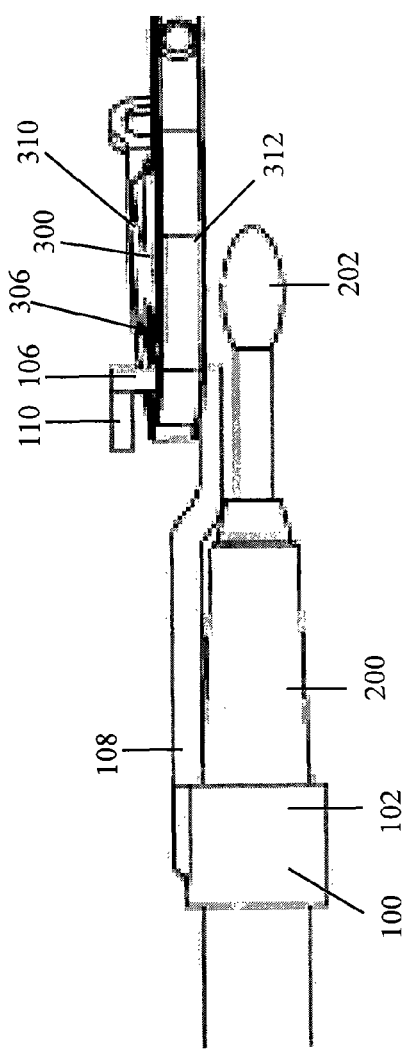
FIG. 8 is a side elevation view of the bur guide attachment of FIG. 6, attached to a burring device and disposed within a controlling device, in accordance with an aspect of the invention.

Referring to FIGS. 6 and 8, member 108 may be configured such that projection 106 is located in an appropriate location relative to bur 202. Thus, in various embodiments, the length of member 108 may be increased so that projection 106 may be located superior and just distal to bur 202. The resection created with a significantly long member 108 may create a shallow resection. In other embodiments member 108 may be shorter, such that projection 106 may be superior but substantially distal to bur 202. In this embodiment, a much deeper resection can be created. Thus, the length of member 108 may be varied in order to create resections of varying depths. Member 108 is shown as generally linear in FIGS. 6-13, however, in alternative embodiments, member 108 may be arcuate or segmented. Arcuate and segmented embodiments of member 108 may be selected by a surgeon to allow the surgeon to have better access to and visibility of a surgical site.

Projection 106 may be typically configured with a particular length, which results in a resection of a particular width. In various embodiments, projection 106 may have a varying length. A longer projection 106 results in a wider resection, while a shorter projection 106 results in a narrower resection. A resection of a desired width and depth can be created by selecting appropriate lengths for member 108 and projection 106.

Figure 9:
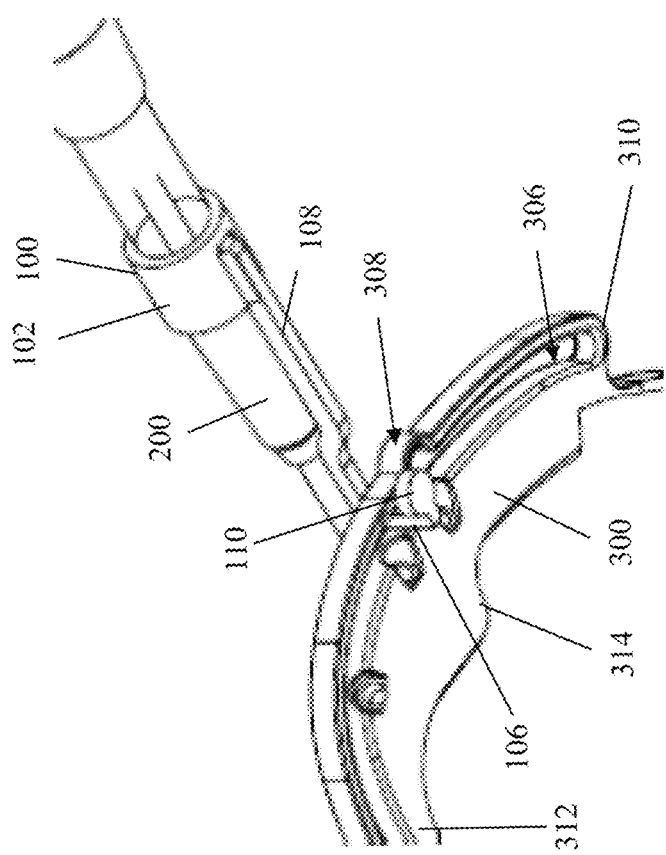
FIG. 9 is a perspective view of the bur guide attachment of FIG. 6, attached to a burring device and disposed within a controlling device, in accordance with an aspect of the invention.
Figure 12:
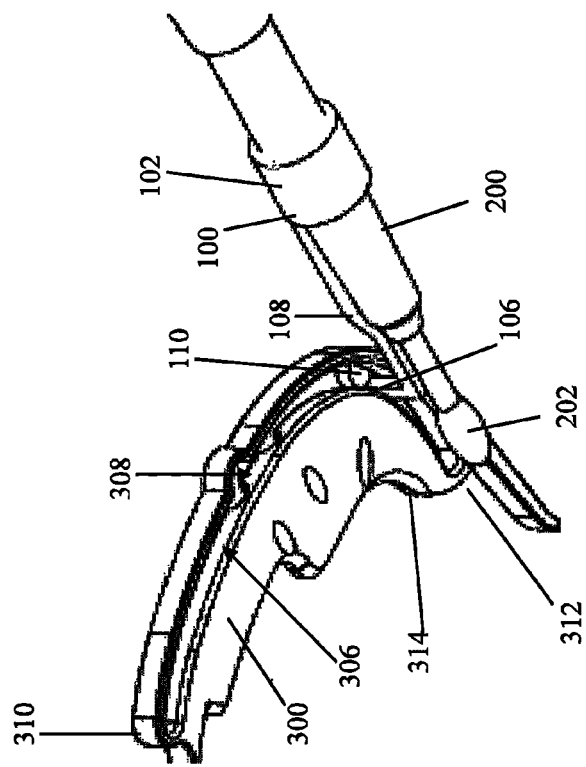
FIG. 12 is a perspective view of the bur guide attachment of FIG. 6, attached to a burring device and disposed within a controlling device, where the burring device has been moved to an second end, in accordance with an aspect of the invention.

Stop 110 is shown as a generally circular object attached to projection 106. In alternative embodiments, stop 110 may be a generally square, polygonal, triangular or other shape. In still another embodiment stop 110 may be generally spherical. Although various embodiments may include stops of different shapes, stops with smooth edges that do not catch on bone or other tissue are preferred. Referring to FIG. 9, stop 110 may be configured to pass through enlargement 308 bur prevent removal of bur attachment guide 100 when stop 110 is not disposed adjacent enlargement 308.

Now referring to FIG. 7, an alternative embodiment of the bur guide attachment 100 is shown where a collet 112 may be provided to secure the bur guide attachment 100 to the burring device 200. In one embodiment, sheath 102 may be screwed into collet 112 in order to secure bur guide attachment 100 to the burring device 200. As described above, the sheath 102 may be capable and configured to prevent rotation of the surgical instrument relative to both the sheath 102 and the patient's anatomy.

Now referring to FIGS. 8 and 9, the bur guide attachment 100 of FIG. 6 is shown disposed about burring device 200. Projection 106 may be generally superior and distal the bur 202 of burring device 200. Projection 106 is shown disposed through a passage 306 formed in controlling device 300. In this embodiment, controlling device 300 may be a guide having a first end 310 and a second end 312. Passage 306 may be formed in controlling device 300 between first end 310 and second end 312. Passage 306 may be designed to receive and retain projection 106. As the burring device 200 is operated, its motion may be guided by controlling device 300, as projection 106 moves along passage 306, thereby preventing unintended motion of burring device 200, and resulting in a resection of the desired dimensions. As shown, stop 110 may be disposed on the opposing side of controlling device 300.

Figure 11:
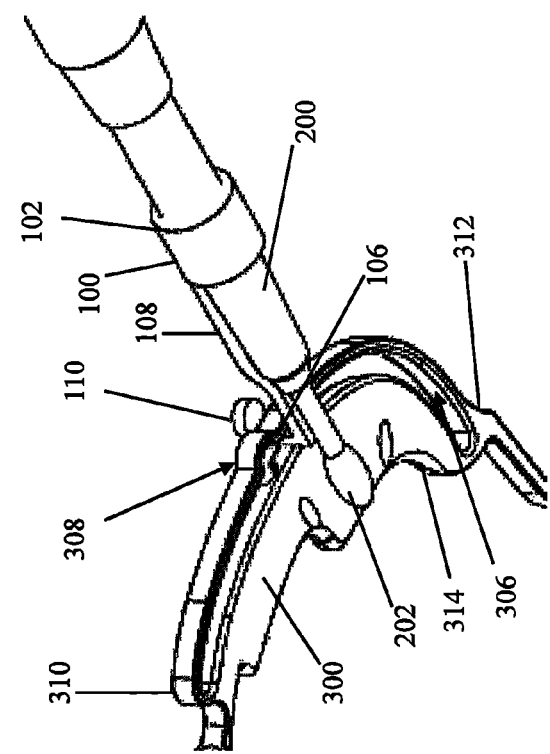
FIG. 11 is a perspective view of the bur guide attachment of FIG. 6, attached to a burring device and disposed within a controlling device, where the burring device has been moved to an intermediary position, in accordance with an aspect of the invention.

Referring to FIG. 9, bur guide attachment 100 has been attached to burring device 200, by disposing sheath 102 about burring device 200. Projection 106, attached to member 108, may be disposed generally superior and distal to bur 202. Controlling device 300 is shown with passage 306 formed therein. An enlargement 308 of passage 306 may be formed in order to accommodate stop 110 and/or projection 106. As shown in FIG. 9, stop 110 may be placed through enlargement 308 to allow projection 106 to be disposed within passage 306. As shown in FIG. 9, enlargement 308 may be formed intermediate first end 310 or second end 312. In alternative embodiments, enlargement 308 of passage 306 may be formed in passage 306 in proximity to first end 310 or second end 312. After stop 110 has been placed through enlargement 308, burring device 200 and bur guide attachment 100, may be moved to first end 310. Projection 106 may come into contact with the end of passage 306, signaling to the user to stop the burring device and reverse direction. The burring device 200 may then be moved from first end 310 toward second end 312 as shown in FIG. 11. The burring device 200 may be moved toward second 312 until projection 106 comes into contact with the end of passage 306 that is closest to second end 312. The user may then return burring device 200 to a position intermediate first end 310 and second end 312. Stop 110 may then be centered over enlargement 308 so that stop 110 may be moved through enlargement 308 and burring device 200 and bur guide attachment 100 may be removed from the operating site. The burring device 200 may be operated and a resection of a patient's anatomy may be performed.

The resection may be repeated by inserting the stop 110 through enlargement 308 in the opposite direction, and the burring device 200 operated and moved from first end 310 to second end 312 in order to create a resection on the opposite side of controlling device 300. The controlling device 300 may then be removed and the surgeon may complete the resection as necessary.

As described above, controlling device 300, in connection with bur guide attachment 100, ensures that a resection of the proper depth is created. More specifically, controlling device 300 prevents burring device 200 from deviating from the desired path. The bur guide attachment 100, and more specifically projection 106 moves along passage 306 as the burring device 200 is operated. The proper length of member 108 creates a resection of the desired depth. The sizing of projection 106 creates a resection of the desired width.

Figure 13:
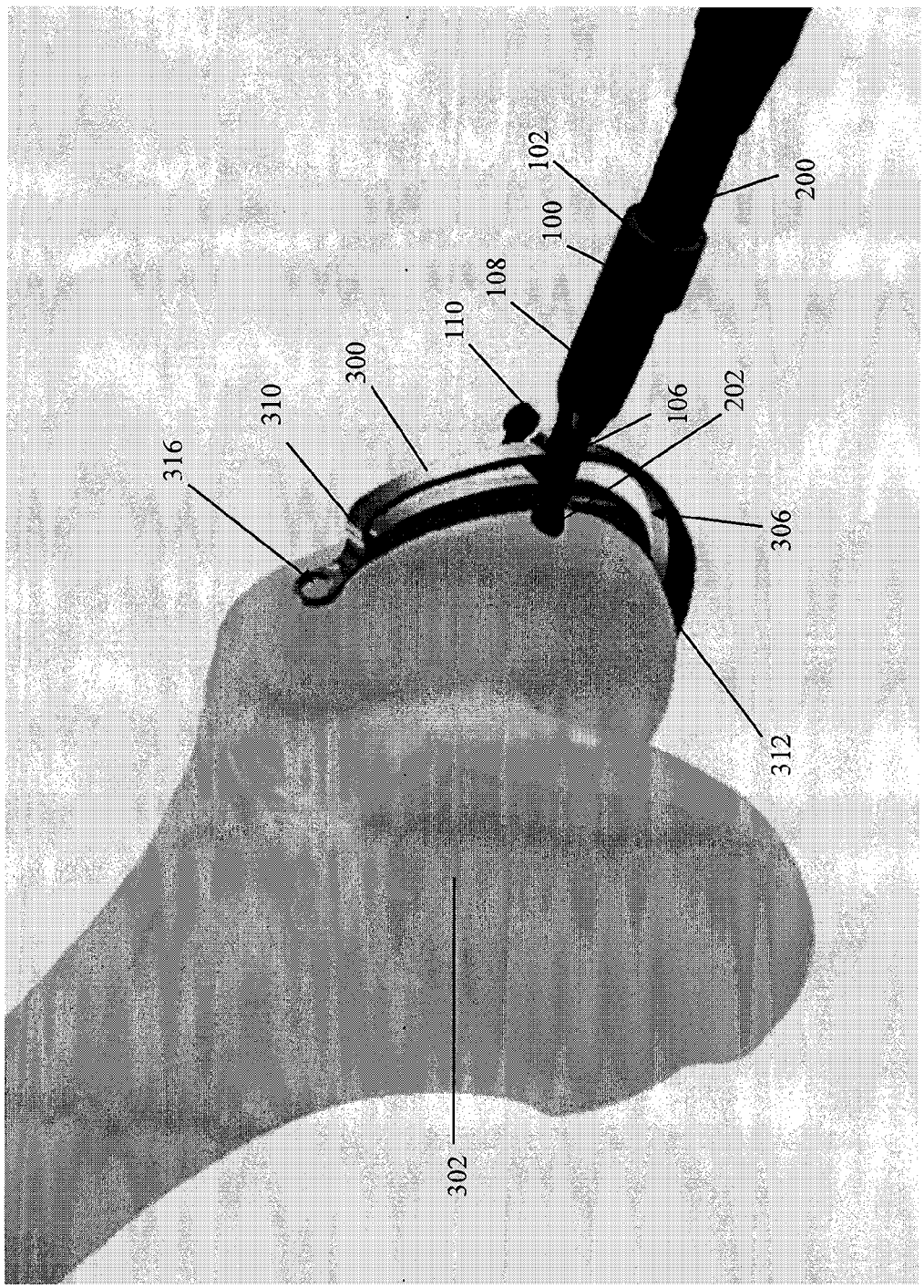
FIG. 13 is a perspective view of the bur guide attachment of FIG. 6 attached to a burring device and disposed within a controlling device, in proximity to a bone, in accordance with an aspect of the invention.

Referring now to FIG. 13, controlling device 300 is shown in proximity to bone 302. A proximal surface 314 (shown in FIGS. 9-12) may be placed in contact with bone 302. Controlling device 300 may include one or more apertures 316. A fixation means (not shown) may be placed through one or more apertures 316 to temporarily affix controlling device 300 to bone 302. The fixation means may be a surgical instrument, screw, bolt, pin wire, glue, cement, or other known means of surgically affixing an object. After the resection has been performed the controlling device 300, burring device 200, and bur guide attachment 100 are all removed from the patient's anatomy.

The embodiment in FIG. 13 shows the burring device 200, bur guide attachment 100 and controlling device 300 in proximity to the distal femur. The burring device 200 may be used, for example, for a unicondylar or total knee replacement surgeries. In alternative embodiments, bur guide attachment 100 and controlling device 300 may be configured to be used with other portions of a patient's anatomy.

The method of performing a surgery may include, selecting a surgical instrument, the surgical instrument may be a burring device or other bone cutting device such as a saw or rasp, selecting an apparatus for controlling the surgical instrument, where the apparatus includes a sheath and a projection, connecting the apparatus for controlling the surgical instrument to the surgical instrument, disposing at least a part of the apparatus within a controlling device, and performing a procedure using the surgical instrument where the surgical instrument is controlled by the controlling device and the apparatus. The method may also include the steps of selecting a controlling device and fastening the controlling device to a patient's anatomy or bone.

Each of the above described embodiments may be comprised of materials suitable to the particular application, including, but not limited to plastic.

While embodiments of the invention have been illustrated and described in detail in the disclosure, the disclosure is to be considered as illustrative and not restrictive in character. All changes and modifications that come within the spirit of the invention are to be considered within the scope of the disclosure.

The invention claimed is:

1. A guide for controlling a surgical instrument, the surgical instrument comprising a cutting member configured to resect a portion of anatomy, the guide comprising:
   a sheath comprising:
      a circular connecting portion with an inner diameter substantially the same as an outer diameter of the surgical instrument, the circular connecting portion configured to receive the surgical instrument;
      at least two distally extending arms connected to the circular connecting portion;
      a ring connected to the distal portion of the at least two distally extending arms; and
      an extension connected to the ring and distally extending along the surgical instrument;
   a guard connected to the distal portion of the extension, the guard extending superior to the cutting member of the surgical instrument; and
   a projection member positioned on a superior surface of the guard, the projection member comprising a generally circular base and a generally circular platform, the platform having a diameter larger than a diameter of the generally circular base.

2. The guide of claim 1, wherein the guard comprises a generally planar inferior surface, the inferior surface configured to move along a surface of a bone and resist rotational forces.

3. The guide of claim 1, wherein the guard extends beyond the cutting member of the surgical instrument in a distal direction.

4. The guide of claim 1, wherein the guard comprises a rounded edge, the rounded edge configured to prevent contact with other surgical implements and reduce the generation of debris during a surgical procedure.

5. The guide of claim 1, wherein the projection member is positioned superior to the cutting member of the surgical instrument.

6. The guide of claim 1, wherein the projection member is positioned in a proximal direction from the cutting member of the surgical instrument.

7. The guide of claim 1, wherein the projection member is positioned in a distal direction from the cutting member of the surgical instrument.

8. The guide of claim 1, wherein the guard has a recessed portion with a depth which receives the cutting member, the depth of the recessed portion determines the depth the cutting member may penetrate into a bone.

9. The guide of claim 1, wherein the sheath comprises a flexible material configured to deform to the shape and size of the surgical instrument.

10. The guide of claim 1, further comprising a controlling member configured to be removably engaged with the projection member and removably attached to a portion of anatomy.

11. The guide of claim 10, wherein the controlling member is a tether comprising a first end and a second end, the first end comprising a first slot formed thereon, the first slot sized to receive the projection member, the second end comprising a second slot, the second slot configured to receive a fastener attached to the portion of anatomy.

12. The guide of claim 11, wherein the tether comprises a length substantially equal to a diameter of a desired resection pathway.

13. The device of claim 11, wherein the tether comprises a flexible material.

14. A guide for a controlling a surgical instrument, the surgical instrument comprising a cutting member configured to resect a portion of anatomy, the guide comprising:
   a generally cylindrical connecting portion with an inner diameter substantially the same as an outer diameter of the surgical instrument, the cylindrical connecting portion configured to receive the surgical instrument;
   at least one distally extending arm connected to the generally cylindrical connecting portion;
   a vertical member attached to the distal end of the distally extending arm;
   a head formed on a superior portion of the vertical member; and
   a frame, comprising:
      at least one aperture configured to receive at least one fastener to secure the frame to a bone;
      at least two rails, the at least two rails forming at least one passageway; and
      at least one aperture in communication with the at least one passageway, the at least one aperture configured to receive the head.

15. The guide of claim 14, wherein the vertical member is positioned in a superior direction from the cutting member.

16. The guide of claim 14, wherein the vertical member is positioned in a proximal direction from the cutting member.

17. The guide of claim 14, wherein the guide is removably coupled to the frame and the vertical member is disposed within the at least one passageway.

18. The guide of claim 14, wherein the at least one distally extending arm comprises a substantially planar member.

19. A method of performing a surgery comprising:
   selecting a surgical instrument comprising a cutting member configured to resect a portion of anatomy;
   selecting a guide comprising:
      a sheath comprising:
         a circular connection portion with an inner diameter substantially the same as an outer diameter of the surgical instrument, the circular connecting portion configured to receive the surgical instrument;
         at least two distally extending arms connected to the circular connecting portion;
         a ring connected to the distal portion of the at least two distally extending arms; and
         an extension connected to the ring and distally extending along the surgical instrument;
      a guard connected to the distal portion of the extension, the guard extending superior to the cutting member of the surgical instrument; and
      a projection member positioned on a superior surface of the guard, the projection member comprising a generally circular base and a generally circular platform, the platform having a diameter larger than a diameter of the generally circular base;
   selecting a tether comprising a first end and a second end, the first end comprising a first slot formed thereon, the first slot sized to receive the projection member, the second end comprising a second slot, the second slot configured to receive a fastener attached to the portion of anatomy;
   disposing the sheath about the surgical instrument;
   inserting the projection member through the first end of the tether;
   inserting the fastener through the second end of the tether; and operating the surgical instrument in a manner controlled by the guide and the tether to perform a resection on the portion of anatomy.

* * * * *